United States Patent [19]

Gironda et al.

[11] Patent Number: 5,461,150
[45] Date of Patent: Oct. 24, 1995

[54] STABILIZATION OF 3-ISOTHIAZOLONE SOLUTIONS

[75] Inventors: Kevin F. Gironda, Alpha, N.J.; George H. Redlich, Norristown, Pa.

[73] Assignee: Rohm and Haas Company, Philadelphia, Pa.

[21] Appl. No.: 355,759

[22] Filed: Dec. 14, 1994

[51] Int. Cl.[6] .......................... A01N 43/80; A61K 7/035; A61K 7/50; C07D 275/03
[52] U.S. Cl. .......................... 548/213; 514/372; 252/106; 424/69
[58] Field of Search .............................. 548/213; 514/372

[56] References Cited

U.S. PATENT DOCUMENTS

Re. 34,185  2/1993  Amick ..................................... 548/213

FOREIGN PATENT DOCUMENTS 2304005  12/1990  Japan .......................................... 43/80

Primary Examiner—Robert Gerstl
Assistant Examiner—Laura R. Cross
Attorney, Agent, or Firm—Michael B. Fein

[57] ABSTRACT

The present invention provides a method of stabilizing solutions of 3-isothiazolone compound(s) selected from the group consisting of 5-chloro-2-methyl-3-isothiazolone, 2-methyl-3-isothiazolone, and mixtures thereof in water free of nitrate or nitrite by the use of extremely low levels of copper ion, and compositions comprising water solutions of 3-isothiazolone compound(s) selected from the group consisting of 5-chloro-2-methyl-3-isothiazolone, 2-methyl-3-isothiazolone, and mixtures thereof, and extremely low levels copper ion.

7 Claims, No Drawings

STABILIZATION OF 3-ISOTHIAZOLONE SOLUTIONS

This invention relates to stabilization of Dilute Solutions of 3-isothiazolones and their use in cosmetics.

Both 5-chloro-2-methyl-3-isothiazolone ("CMI") and 2-methyl-3-isothiazolone ("MI") are well known microbicides which have achieved commercial success in a range of applications. Particularly successful is a mixture of CMI and MI in an approximate ratio of 3:1. These isothiazolones are naturally unstable and much research has been devoted to stabilizing them in various solutions: (1) "Concentrates" which are about 14 to 25% by weight aqueous solutions of CMI and MI; (2) "Dilute Solutions" which are about 0.5 to 5% by weight aqueous solutions of CMI and MI which are designed to be further diluted when added to a locus; and (3) "Use Dilutions" which are the end use dilution in the locus to be protected and comprise substantially less than 1% by weight CMI and MI. Each of these solutions presents special challenges to stabilization of CMI and MI. Concentrates and Dilute Solutions are sold commercially and are diluted and incorporated in loci as Use Dilutions.

1.5% Dilute Solutions are usually stabilized either with high levels magnesium nitrate (23%); with a combination of low levels of magnesium nitrate (1.5–5%) and very low levels of copper nitrate (0.037–0.14% as copper ion); or with a combination of low levels of magnesium nitrate (1.5–5%) and 0.6% hydrogen peroxide. 4% Dilute Solutions of mixtures of CMI and MI are stabilized with both 4.6% magnesium nitrate and 4% copper sulfate.

Amick, U.S. Re. Pat. No. 34,185 teaches that non-aqueous solutions of 3-isothiazolones can be stabilized against chemical decomposition by using organic hydroxylic solvents, such as ethylene glycol. Japanese Kokai 02-304005 discloses non-aqueous compositions of mixtures of CMI and MI in ethylene glycol and an anionic surfactant that comprise low levels of copper ion to protect the isothiazolone against attack by the surfactant. This reference does not teach the applicability of copper ion to stabilize isothiazolones against chemical decomposition in systems that have 100% water as the solvent.

When 3-isothiazolone dilute solutions stabilized with high levels of magnesium nitrate (23%) are added to latices, for example, the high salt level can cause coagulation of the latices. Nitrates also cause problems. There is a concern about nitrates in certain applications where amines may be present because of the possibility of nitosamine formation. Even as little as 0.14% copper nitrate is a concern in some countries due to limits on the amount of copper permitted in water discharge streams.

We have discovered a method of stabilizing a solution of 3-isothiazolone compound(s) selected from the group consisting of CMI, MI, and mixtures thereof in water from chemical decomposition comprising incorporating in said solution 0.02 to 0.0008 parts by weight of copper ion in the form of a copper salt per 1.5 parts by weight of said 3-isothiazolone compound(s), without the need for nitrite, nitrate, or magnesium. These "salt free" extremely low level copper-stabilized compositions are especially useful to protect cosmetic compositions.

The compositions of the invention comprise a solution of 3-isothiazolone compound(s) selected from the group consisting of 5-chloro-2-methyl-3-isothiazolone, 2-methyl-3-isothiazolone and mixtures thereof in water, stabilized with a low level of copper ion in the form of a copper salt other than nitrate or nitrite, the weight ratio of said copper ion to said 3-isothiazolone compound(s) being 0.02:1.5 to 0.0008:1.5, said solution being free of nitrate, nitrite, and magnesium.

The preferred concentration of the 3-isothiazolone compound(s) in solution is 0.5 to 5.0 parts by weight per 100 parts by weight solution. The most preferred concentration of the 3-isothiazolone compound(s) in solution is 1 to 2 parts by weight per 100 parts by weight solution.

The CMI and MI may be used either alone or in admixture. When in admixture, the preferred ratio of CMI to MI is from about 90:10 to 2:98. Especially preferred is a ratio of 75:25 to 80:20.

A wide variety of copper salts are known in the art. Any copper salt which is sufficiently water soluble to provide the desired level of copper ion in solution may be used. Suitable examples are copper sulfate, copper acetate, copper chloride, copper bromide, copper chlorate, copper perchlorate, and the like. Copper sulfate is preferred.

Typically, the ratio of copper ion to 3-isothiazolone compound(s) is from about 1:1000 to about 1:60. Less copper ion is needed at lower 3-isothiazolone concentrations than at higher concentrations. As the concentration of the isothiazolone is increased, proportionally more copper ion is required to achieve the same stability. For example, a ratio of copper ion to 3-isothiazolone compound(s) of 1:1000 is sufficient to stabilize a 1.5% 3-isothiazolone dilute solution, while a ratio of 1:60 is needed for 5% 3-isothiazolone dilute solutions.

The compositions of the invention are prepared by mixing the isothiazolone, water, and copper salt in any order.

The term microbicide includes bactericides, fungicides, and algaecides. Microbicidal or biocidal activity is intended to include both the elimination of and inhibition of growth of microbial organisms, such as bacteria, fungi, and algae.

Uses of these stabilized microbicides are typically at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, these stabilized microbicides may also be used in all applications for which known microbicidal compositions are useful; preferred utilities of the compositions of the invention are to protect wood, latex, adhesive, glue, paper, textile, leather, plastics, cardboard, caulking, feed, cosmetics; e.g. shampoos, conditioners, lotions, and creams; household products; e.g. dish detergents, floor waxes, cleaning products, etc.

Because isothiazolones are so active as microbicides and only low levels of copper ion are required to achieve stabilization, the amount of copper ion in systems being treated will be very low, and therefore it is not likely to interfere with other components in systems requiring protection or with systems to which protected systems will be applied.

It is known in the art that the performance of microbicides may be enhanced by combination with one or more other microbicides. Thus, other known microbicides may be combined advantageously with the composition of this invention.

In the following examples, the 3-isothiazolones used were an approximate 3:1 mixture of CMI and MI (96.5% pure) containing no stabilizer and the level of copper reported in parts per million ("ppm") is the level of copper(II) ion. Samples were considered stable when 80% of CMI remained after 4 weeks storage at 55° C. All samples were analyzed by HPLC with UV detection.

EXAMPLE 1

To each of three 30 ml screw cap, glass vials, samples 1-1, 1-2 and 1-3, were added 0.16 g of 3-isothiazolones. To sample 1-1 were further added 0.008 g of copper sulfate (equivalent to 200 ppm copper ion) and 9.83 g of deionized ("DI") water and to sample 1-2 were added 0.003 g of copper sulfate (equivalent to 77 ppm copper ion) and 9.83 g of DI water. Sample 1-3 was comparative and contained only the 3-isothiazolones and 9.84 g of DI water. These samples contained 1.5% 3-isothiazolones by weight. The samples were capped, manually shaken to dissolve the salts and stored in an oven at 55° C. The samples were analyzed for remaining CMI after 1, 2, 4, and 6 weeks of storage. The results are reported below.

TABLE 1

| Sample | Copper (ppm) | % CMI Remaining | | | |
| --- | --- | --- | --- | --- | --- |
| | | 1 Week | 2 Weeks | 4 Weeks | 6 Weeks |
| 1-1 | 200 | 99 | 98 | 95 | 95 |
| 1-2 | 77 | 100 | 98 | 94 | 94 |
| 1-3* | 0 | 0 | — | — | — |

* = comparative

These data show that low levels of copper stabilize dilute solutions of 3-isothiazolones without the need for additional stabilizers.

EXAMPLE 2

This example demonstrates the stabilizing effect of low levels of copper ion. A 1% $Cu^{+2}$ stock solution was prepared by adding 0.196 g of copper sulfate to 5.0 g DI water in a 30 ml screw cap, glass vial. The samples were prepared by adding 0.16 g of 3-isothiazolones to each of four 30 ml screw cap, glass vials, samples 2-1 to 2-4. To sample 2-1 was further added 9.74 g DI water and 0.10 g of the 1% $Cu^{+2}$ stock solution (equivalent to 100 ppm of copper ion), to sample 2-2 was further added 9.79 g DI water and 0.05 g of the 1% $Cu^{+2}$ stock solution (equivalent to 50 ppm of copper ion), and to sample 2-3 was further added 9.82 g DI water and 0.02 g of the 1% $Cu^{+2}$ stock solution (equivalent to 20 ppm of copper ion). Sample 2-4 was comparative (no copper stabilizer) and only 9.84 g of DI water were added to the sample. All the samples contained 1.5% 3-isothiazolone by weight. The samples were capped, stored in an oven at 55° C. and analyzed for remaining CMI after 1, 2, 3, and 4 weeks of storage. The results are reported below.

TABLE 2

| Sample | Copper (ppm) | % CMI Remaining | | | |
| --- | --- | --- | --- | --- | --- |
| | | 1 Week | 2 Weeks | 3 Weeks | 4 Weeks |
| 2-1 | 100 | 100 | 100 | 98 | 97 |
| 2-2 | 50 | 99 | 98 | 96 | 95 |
| 2-3 | 20 | 99 | 96 | 93 | 92 |
| 2-4* | 0 | 0 | — | — | — |

* = comparative

From these data it can be seen that very low levels of copper ion are sufficient to stabilize dilute solutions of 3-isothiazolones.

EXAMPLE 3

A 0.1% $Cu^{+2}$ stock solution was prepared in a 30 ml screw cap, glass vial by adding 0.038 g of copper sulfate and 9.962 g DI water. The samples were prepared by adding 0.16 g of 3-isothiazolones to each of two 30 ml screw cap, glass vials. To sample 3-1 was further added 0.15 g of the 0.1% $Cu^{+2}$ stock solution (equivalent to 15 ppm of copper ion) and 9.69 g DI water. To sample 3-2 was further added 0.10 g of the 0.1% $Cu^{+2}$ stock solution (equivalent to 10 ppm copper ion) and 9.74 g DI water. Both samples contained 1.5% 3-isothiazolone by weight. The samples were capped, stored in an oven at 55° C. and analyzed for remaining CMI after 2, 3, and 4 weeks of storage. The results are reported below.

TABLE 3

| Sample | Copper (ppm) | % CMI Remaining | | |
| --- | --- | --- | --- | --- |
| | | 2 Weeks | 3 Weeks | 4 Weeks |
| 3-1 | 15 | 93 | 88 | 82 |
| 3-2 | 10 | 92 | 68 | NA |

NA = not analyzed

These data show that a ratio of copper ion to 3-isothiazolone of 1:1000 provides sufficient stability for 1.5% 3-isothiazolone dilute solutions.

EXAMPLE 4

A sample was prepared by adding 2.50 g of the 0.1% $Cu^{+2}$ stock solution prepared in Example 3, 6.98 g DI water and 0.52 g of 3-isothiazolones. This sample contained 5% 3-isothiazolone by weight and 250 ppm of copper ion. The sample was capped, stored in an oven at 55° C. and analyzed after 2, 3, and 4 weeks storage. The results are reported below.

TABLE 4

| Sample | Copper (ppm) | % CMI Remaining | | |
| --- | --- | --- | --- | --- |
| | | 2 Weeks | 3 Weeks | 4 Weeks |
| 4-1 | 250 | 90 | 84 | 65 |

These data show that higher ratios of copper ion to 3-isothiazolone are needed to sufficiently stabilize 5% 3-isothiazolone dilute soltions than are needed for 1.5% 3-isothiazolone dilute solutions.

EXAMPLE 5

This example demonstrates the superior stabilizing effects of low levels of copper ion over the prior art. A dilute copper sulfate solution was prepared by dissolving 0.0196 g of copper sulfate in 4.984 g DI water in a 30 ml glass vial to yield a 0.10% copper ion solution. Sample 5-1 was prepared by adding 0.77 g of the dilute copper sulfate solution to a 30 ml screw cap, glass vial along with 9.07 g DI water and 0.16 g of 3-isothiazolones. This gave a sample with 77 ppm copper ion and 1.5% 3-isothiazolones. Sample 5-2 was prepared by adding 2.77 g of magnesium nitrate (64% anhydrous), 5.99 g DI water and 1.24 g 3-isothiazolones to a 30 ml screw cap, glass vial. This sample represented a commercial concentrate and had 12% 3-isothiazolones and 16% magnesium nitrate as stabilizer. Sample 5-3 was prepared by adding 0.26 g magnesium nitrate (64% anhydrous), 9.58 g DI water and 0.16 g 3-isothiazolones to a 30 ml screw cap, glass vial. This sample represented a dilute solution made by simply diluting a commercial concentrate sample and had 1.5% 3-isothiazolones and 1.5% magnesium nitrate as stabilizer. Sample 5-4 was prepared by adding 3.98 g of magnesium nitrate (64% anhydrous), 5.86 g of DI water and 0.16 g 3-isothiazolones to a 30 ml screw cap, glass vial. This sample represented a commercial sample of a stable dilute solution and had 1.5 % 3-isothiazolones and 23% magnesium nitrate as stabilizer.

All samples were capped, shaken, and stored in an oven at 40° C. The samples were analyzed for remaining CMI after 1, 2, 3, and 4 weeks storage. The results are reported below.

TABLE 5

| Sample | % ITA | % Mg (NO$_3$)$_2$ | % CMI Remaining | | | |
|---|---|---|---|---|---|---|
| | | | 1 Week | 2 Weeks | 3 Weeks | 4 Weeks |
| 5-1 | 1.5 | — | 100 | 100 | 96 | 99 |
| 5-2* | 12 | 16 | 101 | 100 | 96 | 95 |
| 5-3* | 1.5 | 1.5 | 80 | 68 | 57 | 52 |
| 5-4* | 1.5 | 23 | 101 | 100 | 96 | 102 |

* = comparative

These data show that when a 3-isothiazolone concentrate sample is diluted to form a dilute solution, additional stabilizer is required to achieve the desired stability. It was unexpected that such a low level of copper ion would be able to stabilize an isothiazolone dilute solution absent other stabilizers, such as magnesium nitrate.

EXAMPLE 6

This example demonstrates the effect of higher levels of copper ion as a stabilizer for 3-isothiazolones. Sample 6-1 was prepared by adding 0.59 g copper sulfate (64% anhydrous), 8.17 g DI water and 1.24 g 3-isothiazolone to a 30 ml glass, screw cap vial. Sample 6-2 was prepared by adding 8.76 g DI water and 1.24 g 3-isothiazolone to a 30 ml glass, screw cap vial. The vials were capped, shaken and stored in an oven at 40° C. Sample 6-1 contained 12% 3-isothiazolone and 1.5% (15000 ppm) Cu$^{+2}$ ion. Sample 6-2 contained 12% 3-isothiazolone and no copper. The samples were analyzed at various time points and the results reported below.

TABLE 6

| Sample | ppm Cu$^{+2}$ | % CMI Remaining | | | |
|---|---|---|---|---|---|
| | | 1 Week | 2 Weeks | 3 Weeks | 4 Weeks |
| 6-1 | 15000 | 16 | 1 | NA | NA |
| 6-2 | — | 96 | 87 | 80 | 73 |

NA = not analyzed

These results show that higher levels of copper ion are antagonistic to the stability of the 3-isothiazolones.

EXAMPLE 7 (COMPARATIVE)

This example demonstrates that non-aqueous, ethylene glycol solutions of 3-isothiazolones are stable. Sample 7-1 was prepared by adding 8.76 g ethylene glycol and 1.24 g 3-isothiazolone to a 30 ml glass, screw cap vial. Sample 7-2 was prepared by adding 9.84 g ethylene glycol and 0.16 g 3-isothiazolone to a 30 ml glass, screw cap vial. The vials were capped, shaken and stored in an oven at 40° C. Sample 7-1 contained 12% 3-isothiazolone in ethylene glycol with no water or copper ion. Sample 7-2 contained 1.5% 3-isothiazolone and no water or copper ion. The samples were analyzed at various time points and the results reported below.

TABLE 7

| Sample | % CMI Remaining | | | |
|---|---|---|---|---|
| | 1 Week | 2 Weeks | 3 Weeks | 4 Weeks |
| 7-1 | 102 | 104 | 106 | 104 |
| 7-2 | 101 | 100 | 92 | 89 |

These data show that non-aqueous, ethylene glycol solutions of 3-isothiazolones are stable.

We claim:

1. Compostion comprising a solution of 3-isothiazolone compound(s) selected from the group consisting of 5-chloro-2-methyl-3-isothiazolone, 2-methyl- 3-isothiazolone and mixtures thereof in a solvent system consisting essentially of water, stabilized with a low level of copper ion in the form of a copper salt other than nitrate or nitrite, the weight ratio of said copper ion to said 3-isothiazolone compound(s) being 0.02:1.5 to 0.0008:1.5, said solution being free of nitrate, nitrite, and magnesium.

2. Composition according to claim 1 wherein the concentration of said 3-isothiazolone compound(s) in solution is 0.5 to 5.0 parts by weight per 100 parts by weight solution.

3. Composition according to claim 2 wherein said concentration is 1 to 2 parts by weight per 100 parts by weight solution.

4. Composition according to claim 1 wherein said copper salt is selected from the group consisting of copper sulfate, copper acetate, copper chloride, copper bromide, copper chlorate, and copper perchlorate.

5. Method of stabilizing a solution of 3-isothiazolone compound(s) selected from the group consisting of 5-chloro-2-methyl-3-isothiazolone, 2-methyl- 3-isothiazolone and mixtures thereof in a solvent system consisting essentially of water from chemical decomposition comprising incorporating in said solution 0.02 to 0.0008 parts by weight of copper ion in the form of a copper salt per 1.5 parts by weight of said 3-isothiazolone compound(s), provided that no nitrite, nitrate or magnesium is incorporated or present in said water solution.

6. Method according to claim 5 wherein the concentration of said 3-isothiazolone compound(s) in water is 0.5 to 5.0 parts by weight per 100 parts by weight solution.

7. Method according to claim 5 wherein said copper salt is selected from the group consisting of copper sulfate, copper acetate, copper chloride, copper bromide, copper chlorate, and copper perchlorate.

* * * * *